(12) United States Patent
Markle et al.

(10) Patent No.: US 8,512,245 B2
(45) Date of Patent: Aug. 20, 2013

(54) SENSOR FOR PERCUTANEOUS INTRAVASCULAR DEPLOYMENT WITHOUT AN INDWELLING CANNULA

(75) Inventors: David R. Markle, Berwyn, PA (US); William H. Markle, Laguna Niguel, CA (US)

(73) Assignee: Glumetrics, Inc., Irvine, CA (US)

( * ) Notice: Subject to any disclaimer, the term of this patent is extended or adjusted under 35 U.S.C. 154(b) by 1161 days.

(21) Appl. No.: 12/424,902

(22) Filed: Apr. 16, 2009

(65) Prior Publication Data
US 2009/0264719 A1 Oct. 22, 2009

Related U.S. Application Data

(60) Provisional application No. 61/045,887, filed on Apr. 17, 2008.

(51) Int. Cl.
- A61B 5/1459 (2006.01)
- A61B 5/145 (2006.01)
- A61B 17/34 (2006.01)

(52) U.S. Cl.
USPC ............... 600/365; 600/309; 600/316

(58) Field of Classification Search
USPC .................................. 600/316, 309
See application file for complete search history.

(56) References Cited

U.S. PATENT DOCUMENTS

| | | |
|---|---|---|
| 1,120,700 A | 12/1914 | Ehrlich |
| 1,334,901 A | 3/1920 | Higdon |
| 2,112,244 A | 3/1938 | Jurist |
| 2,274,551 A | 2/1942 | Kenyon et al. |
| 2,496,151 A | 1/1950 | Dawson et al. |
| 2,812,524 A | 11/1957 | Pruitt |
| 3,011,293 A | 12/1961 | Rado |
| 3,302,219 A | 2/1967 | Harris |
| 3,488,098 A | 1/1970 | Sobczak |
| 3,659,586 A | 5/1972 | Johns et al. |
| 3,795,239 A | 3/1974 | Eberhard et al. |
| 3,827,089 A | 8/1974 | Grow |
| 3,865,548 A | 2/1975 | Padawer |
| 3,874,010 A | 4/1975 | Geary |
| 3,884,225 A | 5/1975 | Witter |

(Continued)

FOREIGN PATENT DOCUMENTS

| | | |
|---|---|---|
| CN | 85108331 | 6/1987 |
| CS | 7707425 | 2/1980 |

(Continued)

OTHER PUBLICATIONS

Bolton C F. 1999 Acute Weakness. In: Oxford Textbook of Critical Care; Eds. Webb A R, Shapiro M J, Singer M, Suter P M; Oxford Medical Publications, Oxford UK; pp. 490-495.
Check, W., "ICUs tighten belts on blood glucose levels", Cap Today, Feb. 2005, in 7 pages, vol. 19-2.
EPO Exam Report re EP App. No. 08 728 399.0, dated Dec. 7, 2010.
EPO Office Action re App. No. 07 799 791.4 dated Jan. 29, 2010.

(Continued)

*Primary Examiner* — Sean Dougherty
*Assistant Examiner* — Michael C Stout
(74) *Attorney, Agent, or Firm* — Knobbe Martens Olson & Bear, LLP (57) ABSTRACT

The present invention relates to a sensor for percutaneous insertion and intravascular residence without an indwelling cannula. In preferred embodiments, a glucose sensor is inserted into a blood vessel using a removable cannula. After the cannula is removed, the glucose sensor remains within the blood vessel by itself and forms a seal with the patient's tissue.

17 Claims, 6 Drawing Sheets

(56) References Cited

U.S. PATENT DOCUMENTS

| | | | |
|---|---|---|---|
| 3,895,403 A | 7/1975 | Davis | |
| 3,905,888 A | 9/1975 | Mindt et al. | |
| 3,909,504 A | 9/1975 | Browne | |
| 3,924,281 A | 12/1975 | Gibbs | |
| 3,930,580 A | 1/1976 | Bazell et al. | |
| 3,996,345 A | 12/1976 | Ullman | |
| 4,003,707 A | 1/1977 | Lübbers et al. | |
| 4,041,932 A | 8/1977 | Fostick | |
| 4,094,578 A | 6/1978 | DiVita et al. | |
| 4,180,879 A | 1/1980 | Mann | |
| 4,197,853 A | 4/1980 | Parker | |
| 4,200,110 A | 4/1980 | Peterson et al. | |
| 4,245,645 A | 1/1981 | Arseneault et al. | |
| 4,269,605 A | 5/1981 | Dean et al. | |
| 4,306,562 A | 12/1981 | Osborne | |
| 4,307,933 A | 12/1981 | Palmer et al. | |
| 4,308,254 A | 12/1981 | Tayot et al. | |
| 4,344,438 A | 8/1982 | Schultz | |
| 4,345,606 A * | 8/1982 | Littleford | 607/122 |
| 4,358,851 A | 11/1982 | Scilfres et al. | |
| 4,361,918 A | 12/1982 | Roisseth | |
| 4,371,374 A | 2/1983 | Cerami et al. | |
| 4,459,712 A | 7/1984 | Pathan | |
| 4,465,335 A | 8/1984 | Eppes | |
| 4,469,357 A | 9/1984 | Martin | |
| 4,474,431 A | 10/1984 | Bricheno | |
| 4,476,870 A | 10/1984 | Peterson et al. | |
| 4,490,867 A | 1/1985 | Gabrielson | |
| 4,495,293 A | 1/1985 | Shaffar | |
| 4,502,169 A | 3/1985 | Persson | |
| RE31,879 E | 5/1985 | Lübbers et al. | |
| 4,528,616 A | 7/1985 | Koppensteiner | |
| 4,548,907 A | 10/1985 | Seitz et al. | |
| 4,557,900 A | 12/1985 | Heitzmann | |
| 4,560,248 A | 12/1985 | Cramp et al. | |
| 4,568,444 A | 2/1986 | Nakamura et al. | |
| 4,600,310 A | 7/1986 | Cramp et al. | |
| 4,621,049 A | 11/1986 | Wang | |
| 4,629,451 A | 12/1986 | Winters et al. | |
| 4,636,144 A | 1/1987 | Abe et al. | |
| 4,649,271 A | 3/1987 | Hök et al. | |
| 4,650,472 A | 3/1987 | Bates | |
| 4,654,031 A * | 3/1987 | Lentz | 604/168.01 |
| 4,659,817 A | 4/1987 | Gallop et al. | |
| 4,675,925 A | 6/1987 | Littleton | |
| 4,684,538 A | 8/1987 | Klemarczyk | |
| RE32,514 E | 10/1987 | Steklenski | |
| 4,703,756 A | 11/1987 | Gough et al. | |
| 4,707,056 A | 11/1987 | Bittner | |
| 4,710,623 A | 12/1987 | Lipson et al. | |
| 4,727,730 A | 3/1988 | Boiarski et al. | |
| 4,737,153 A | 4/1988 | Shimamura et al. | |
| 4,744,618 A | 5/1988 | Mahlein | |
| 4,746,751 A | 5/1988 | Oviatt | |
| 4,750,795 A | 6/1988 | Blotekjaer | |
| 4,751,918 A | 6/1988 | Bernard et al. | |
| 4,754,538 A | 7/1988 | Stewart, Jr. et al. | |
| 4,776,047 A | 10/1988 | DiMatteo | |
| 4,785,814 A | 11/1988 | Kane | |
| 4,794,619 A | 12/1988 | Tregay | |
| 4,796,633 A | 1/1989 | Zwirkoski | |
| 4,798,738 A | 1/1989 | Yafuso et al. | |
| 4,801,187 A | 1/1989 | Elbert et al. | |
| 4,803,049 A | 2/1989 | Hirschfeld et al. | |
| 4,816,130 A | 3/1989 | Karakelle et al. | |
| 4,820,636 A | 4/1989 | Hill et al. | |
| 4,821,738 A * | 4/1989 | Iwasaki et al. | 600/578 |
| 4,822,127 A | 4/1989 | Kamiya et al. | |
| 4,833,091 A | 5/1989 | Leader et al. | |
| 4,838,269 A | 6/1989 | Robinson et al. | |
| 4,846,543 A | 7/1989 | Kapany et al. | |
| 4,851,195 A | 7/1989 | Matthews et al. | |
| 4,854,321 A | 8/1989 | Boiarski | |
| 4,861,728 A | 8/1989 | Wagner | |
| 4,872,226 A | 10/1989 | Lonardo | |
| 4,872,759 A | 10/1989 | Stich-Baumeister | |
| 4,886,338 A | 12/1989 | Yafuso et al. | |
| 4,889,407 A | 12/1989 | Markle et al. | |
| 4,903,707 A | 2/1990 | Knute et al. | |
| 4,906,232 A | 3/1990 | Reynolds | |
| 4,923,273 A | 5/1990 | Taylor | |
| 4,927,222 A | 5/1990 | Kamiya et al. | |
| 4,937,901 A | 7/1990 | Brennan | |
| 4,939,801 A | 7/1990 | Schaal et al. | |
| 4,941,308 A | 7/1990 | Grabenkort et al. | |
| 4,943,364 A | 7/1990 | Koch et al. | |
| 4,946,038 A | 8/1990 | Eaton | |
| 4,955,862 A | 9/1990 | Sepetka | |
| 4,960,412 A | 10/1990 | Fink | |
| 4,966,597 A | 10/1990 | Cosman | |
| 5,000,901 A | 3/1991 | Iyer et al. | |
| 5,005,576 A | 4/1991 | Günther | |
| 5,007,704 A | 4/1991 | McCartney | |
| 5,012,809 A | 5/1991 | Shulze | |
| 5,018,225 A | 5/1991 | Fergni et al. | |
| 5,030,420 A | 7/1991 | Bacon | |
| 5,047,208 A | 9/1991 | Schweitzer et al. | |
| 5,047,627 A | 9/1991 | Yim et al. | |
| 5,054,497 A | 10/1991 | Kapp et al. | |
| 5,068,931 A | 12/1991 | Smith | |
| 5,069,674 A | 12/1991 | Fearnot et al. | |
| 5,082,112 A | 1/1992 | Dunklee | |
| 5,093,266 A | 3/1992 | Leader et al. | |
| 5,098,618 A | 3/1992 | Zelez | |
| 5,104,388 A | 4/1992 | Quackenbush | |
| 5,108,502 A | 4/1992 | Pawlowski et al. | |
| 5,109,452 A | 4/1992 | Selvin et al. | |
| 5,114,676 A | 5/1992 | Leiner et al. | |
| 5,119,463 A | 6/1992 | Vurek | |
| 5,137,833 A | 8/1992 | Russell | |
| 5,141,497 A * | 8/1992 | Erskine | 604/164.05 |
| 5,162,130 A | 11/1992 | McLaughlin | |
| 5,166,990 A | 11/1992 | Riccitelli et al. | |
| 5,167,715 A | 12/1992 | Kalafala et al. | |
| 5,168,587 A | 12/1992 | Shutes | |
| 5,175,016 A | 12/1992 | Yafuso et al. | |
| 5,176,882 A | 1/1993 | Gray et al. | |
| 5,178,267 A | 1/1993 | Grabenkort et al. | |
| 5,180,376 A * | 1/1993 | Fischell | 604/524 |
| 5,182,353 A | 1/1993 | Hui et al. | |
| 5,185,263 A | 2/1993 | Kroneis et al. | |
| 5,217,691 A | 6/1993 | Greene et al. | |
| 5,230,031 A | 7/1993 | Markle | |
| 5,246,109 A | 9/1993 | Markle et al. | |
| 5,246,441 A | 9/1993 | Ross et al. | |
| 5,257,338 A | 10/1993 | Markle | |
| 5,262,037 A | 11/1993 | Markle et al. | |
| 5,279,596 A | 1/1994 | Castaneda et al. | |
| 5,280,130 A | 1/1994 | Markle et al. | |
| 5,280,548 A | 1/1994 | Atwater et al. | |
| 5,284,154 A * | 2/1994 | Raymond et al. | 600/554 |
| 5,286,294 A | 2/1994 | Ebi et al. | |
| 5,290,266 A | 3/1994 | Rohling et al. | |
| 5,302,731 A | 4/1994 | Pitner et al. | |
| 5,305,740 A | 4/1994 | Kolobow | |
| 5,310,471 A | 5/1994 | Markle et al. | |
| 5,312,344 A | 5/1994 | Grinfeld | |
| 5,322,513 A | 6/1994 | Walker | |
| 5,334,157 A * | 8/1994 | Klein et al. | 604/160 |
| 5,354,448 A | 10/1994 | Markle et al. | |
| 5,357,732 A | 10/1994 | Markle et al. | |
| 5,361,758 A | 11/1994 | Hall et al. | |
| 5,380,304 A | 1/1995 | Parker | |
| 5,389,217 A | 2/1995 | Singer | |
| 5,409,469 A * | 4/1995 | Schaerf | 604/524 |
| 5,503,770 A | 4/1996 | James et al. | |
| 5,511,408 A | 4/1996 | Yoshioka et al. | |
| 5,511,547 A | 4/1996 | Markle et al. | |
| 5,512,246 A | 4/1996 | Russell et al. | |
| 5,545,179 A | 8/1996 | Williamson, IV | |
| 5,558,714 A | 9/1996 | Watanabe et al. | |
| 5,569,186 A | 10/1996 | Lord et al. | |
| 5,596,988 A | 1/1997 | Markle et al. | |
| 5,618,587 A | 4/1997 | Markle et al. | |

| Patent No. | Date | Name | Ref |
|---|---|---|---|
| 5,622,259 A | 4/1997 | Church | |
| 5,634,911 A | 6/1997 | Hermann et al. | |
| 5,643,212 A | 7/1997 | Coutre et al. | |
| 5,658,264 A | 8/1997 | Samson | |
| 5,669,920 A | 9/1997 | Conley et al. | |
| 5,676,784 A | 10/1997 | McGaffigan | |
| D388,418 S | 12/1997 | Polson et al. | |
| 5,700,253 A | 12/1997 | Parker | |
| 5,702,373 A | 12/1997 | Samson | |
| 5,747,666 A | 5/1998 | Willis | |
| 5,755,704 A | 5/1998 | Lunn | |
| 5,763,238 A | 6/1998 | James et al. | |
| 5,797,876 A | 8/1998 | Spears et al. | |
| 5,810,985 A | 9/1998 | Bao et al. | |
| 5,827,242 A | 10/1998 | Follmer et al. | |
| 5,891,100 A | 4/1999 | Fleckenstein | |
| 5,891,114 A | 4/1999 | Chien et al. | |
| 5,922,612 A | 7/1999 | Alder et al. | |
| 5,947,940 A | 9/1999 | Beisel | |
| 5,951,929 A | 9/1999 | Wilson | |
| 5,954,651 A | 9/1999 | Berg et al. | |
| 6,002,954 A | 12/1999 | Van Antwerp et al. | |
| 6,011,984 A | 1/2000 | Van Antwerp et al. | |
| 6,019,736 A | 2/2000 | Avellanet et al. | |
| 6,152,933 A | 11/2000 | Werp et al. | |
| 6,156,010 A * | 12/2000 | Kuracina et al. | 604/168.01 |
| 6,175,752 B1 | 1/2001 | Say et al. | |
| 6,187,130 B1 | 2/2001 | Berard et al. | |
| 6,200,301 B1 | 3/2001 | Pfeiffer et al. | |
| 6,273,874 B1 * | 8/2001 | Parris | 604/198 |
| 6,304,766 B1 | 10/2001 | Colvin, Jr. | |
| 6,319,540 B1 | 11/2001 | Van Antwerp et al. | |
| 6,361,508 B1 * | 3/2002 | Johnson et al. | 600/595 |
| 6,363,273 B1 | 3/2002 | Mastrorio et al. | |
| 6,370,406 B1 * | 4/2002 | Wach et al. | 600/310 |
| 6,375,627 B1 | 4/2002 | Mauze | |
| 6,387,672 B1 | 5/2002 | Arimori et al. | |
| 6,464,849 B1 | 10/2002 | Say | |
| 6,544,212 B2 | 4/2003 | Galley et al. | |
| 6,584,335 B1 * | 6/2003 | Haar et al. | 600/322 |
| 6,585,665 B1 | 7/2003 | Chapman et al. | |
| 6,602,702 B1 | 8/2003 | McDevitt et al. | |
| 6,623,490 B1 | 9/2003 | Crane et al. | |
| 6,627,177 B2 | 9/2003 | Singaram et al. | |
| 6,653,141 B2 | 11/2003 | Singaram et al. | |
| 6,663,595 B2 * | 12/2003 | Spohn et al. | 604/161 |
| 6,682,938 B1 | 1/2004 | Satcher, Jr. et al. | |
| 6,702,972 B1 | 3/2004 | Markle | |
| 6,711,423 B2 | 3/2004 | Colvin, Jr. | |
| 6,766,183 B2 | 7/2004 | Walsh et al. | |
| 6,794,195 B2 | 9/2004 | Colvin, Jr. | |
| 6,800,451 B2 | 10/2004 | Daniloff et al. | |
| 6,804,544 B2 | 10/2004 | Van Antwerp et al. | |
| D525,632 S | 7/2006 | Jost et al. | |
| 7,181,260 B2 | 2/2007 | Gutierrez | |
| 7,216,001 B2 * | 5/2007 | Hacker et al. | 607/63 |
| D544,871 S | 6/2007 | Lim et al. | |
| 7,226,414 B2 | 6/2007 | Ballerstadt | |
| 7,229,450 B1 * | 6/2007 | Chitre et al. | 606/129 |
| D550,242 S | 9/2007 | Niijima | |
| D550,245 S | 9/2007 | Niijima | |
| 7,277,740 B2 * | 10/2007 | Rohleder et al. | 600/316 |
| D559,264 S | 1/2008 | Niijima | |
| D560,224 S | 1/2008 | Park et al. | |
| 7,353,055 B2 | 4/2008 | Hogan | |
| 7,358,094 B2 | 4/2008 | Bell et al. | |
| 7,381,938 B2 | 6/2008 | Kobayashi et al. | |
| 7,390,462 B2 | 6/2008 | Rao et al. | |
| 7,417,164 B2 | 8/2008 | Suri | |
| D580,950 S | 11/2008 | Steele et al. | |
| D582,939 S | 12/2008 | Neuhaus | |
| 7,470,420 B2 | 12/2008 | Singaram et al. | |
| D592,223 S | 5/2009 | Neuhaus | |
| 7,615,007 B2 | 11/2009 | Shults et al. | |
| D610,065 S | 2/2010 | Park | |
| 7,751,863 B2 | 7/2010 | Markle et al. | |
| D626,143 S | 10/2010 | Karten et al. | |
| 7,824,918 B2 | 11/2010 | Suri | |
| 7,829,341 B2 | 11/2010 | Gamsey et al. | |
| 7,879,024 B2 * | 2/2011 | Thorstenson et al. | 604/529 |
| 7,939,664 B2 | 5/2011 | Gamsey et al. | |
| 7,959,577 B2 * | 6/2011 | Schmitz et al. | 600/554 |
| 7,981,058 B2 * | 7/2011 | Akay | 600/595 |
| 8,088,097 B2 | 1/2012 | Markle et al. | |
| 2002/0018843 A1 | 2/2002 | Van Antwerp et al. | |
| 2002/0026108 A1 | 2/2002 | Colvin, Jr. | |
| 2002/0107178 A1 | 8/2002 | Van Den Berghe | |
| 2002/0128546 A1 | 9/2002 | Silver | |
| 2002/0193672 A1 | 12/2002 | Walsh et al. | |
| 2003/0013974 A1 | 1/2003 | Natarajan et al. | |
| 2003/0028089 A1 | 2/2003 | Galley et al. | |
| 2004/0028612 A1 | 2/2004 | Singaram et al. | |
| 2004/0072358 A1 | 4/2004 | Ballerstadt | |
| 2004/0077969 A1 * | 4/2004 | Onda et al. | 600/547 |
| 2004/0136924 A1 | 7/2004 | Boyd et al. | |
| 2004/0219535 A1 | 11/2004 | Bell et al. | |
| 2004/0230138 A1 * | 11/2004 | Inoue et al. | 600/595 |
| 2004/0243018 A1 * | 12/2004 | Organ et al. | 600/547 |
| 2004/0260158 A1 | 12/2004 | Hogan | |
| 2004/0260162 A1 * | 12/2004 | Rohleder et al. | 600/342 |
| 2004/0267203 A1 * | 12/2004 | Potter et al. | 604/164.05 |
| 2005/0054975 A1 * | 3/2005 | Patel et al. | 604/93.01 |
| 2005/0090014 A1 | 4/2005 | Rao et al. | |
| 2005/0130249 A1 | 6/2005 | Parris et al. | |
| 2005/0233465 A1 | 10/2005 | Miller | |
| 2005/0240086 A1 * | 10/2005 | Akay | 600/300 |
| 2005/0241959 A1 | 11/2005 | Ward et al. | |
| 2005/0267326 A1 * | 12/2005 | Loeb et al. | 600/102 |
| 2005/0283204 A1 * | 12/2005 | Buhlmann et al. | 607/48 |
| 2006/0083688 A1 * | 4/2006 | Singaram et al. | 424/9.6 |
| 2006/0084854 A1 | 4/2006 | Cho et al. | |
| 2006/0105174 A1 | 5/2006 | Aller et al. | |
| 2006/0135888 A1 * | 6/2006 | Mimnagh-Kelleher et al. | 600/595 |
| 2006/0189863 A1 | 8/2006 | Peyser et al. | |
| 2006/0189979 A1 * | 8/2006 | Esch et al. | 606/49 |
| 2006/0195042 A1 | 8/2006 | Flaherty et al. | |
| 2006/0270949 A1 * | 11/2006 | Mathie et al. | 600/595 |
| 2006/0287600 A1 | 12/2006 | McEowen | |
| 2007/0038155 A1 * | 2/2007 | Kelly et al. | 600/595 |
| 2007/0060872 A1 | 3/2007 | Hall et al. | |
| 2007/0100356 A1 * | 5/2007 | Lucatero et al. | 606/139 |
| 2007/0123775 A1 | 5/2007 | Meyer et al. | |
| 2007/0175828 A1 | 8/2007 | Goedje et al. | |
| 2007/0256477 A1 | 11/2007 | Moor | |
| 2007/0265675 A1 * | 11/2007 | Lund et al. | 607/41 |
| 2008/0001091 A1 | 1/2008 | Kobayashi et al. | |
| 2008/0009687 A1 | 1/2008 | Smith et al. | |
| 2008/0027245 A1 | 1/2008 | Suri | |
| 2008/0086042 A1 * | 4/2008 | Brister et al. | 600/347 |
| 2008/0154107 A1 | 6/2008 | Jina | |
| 2008/0183061 A1 | 7/2008 | Goode et al. | |
| 2008/0187655 A1 | 8/2008 | Markle et al. | |
| 2008/0188722 A1 | 8/2008 | Markle et al. | |
| 2008/0188725 A1 | 8/2008 | Markle et al. | |
| 2008/0287761 A1 * | 11/2008 | Hayter et al. | 600/365 |
| 2008/0305009 A1 | 12/2008 | Gamsey et al. | |
| 2008/0305506 A1 | 12/2008 | Suri | |
| 2008/0306363 A1 * | 12/2008 | Chaiken et al. | 600/310 |
| 2008/0312560 A1 * | 12/2008 | Jamsen et al. | 600/595 |
| 2009/0018418 A1 | 1/2009 | Markle et al. | |
| 2009/0061528 A1 | 3/2009 | Suri | |
| 2009/0062696 A1 * | 3/2009 | Nathan et al. | 600/595 |
| 2009/0076336 A1 * | 3/2009 | Mazar et al. | 600/300 |
| 2009/0081803 A1 | 3/2009 | Gamsey et al. | |
| 2009/0171381 A1 * | 7/2009 | Schmitz et al. | 606/167 |
| 2009/0177143 A1 | 7/2009 | Markle et al. | |
| 2009/0192416 A1 * | 7/2009 | Ernst et al. | 600/595 |
| 2009/0228068 A1 * | 9/2009 | Buhlmann et al. | 607/48 |
| 2009/0275815 A1 | 11/2009 | Bickoff et al. | |
| 2010/0274110 A1 | 10/2010 | Markle | |
| 2010/0292617 A1 * | 11/2010 | Lei et al. | 600/595 |
| 2011/0171742 A1 | 7/2011 | Gamsey | |
| 2012/0116191 A1 | 5/2012 | Markle | |

FOREIGN PATENT DOCUMENTS

| | | |
|---|---|---|
| DE | 3036868 | 5/1982 |
| DE | 3509262 | 3/1985 |

| | | |
|---|---|---|
| DE | 3720736 | 1/1989 |
| DE | 195 02 183 | 8/1996 |
| DE | 298 17 986 | 2/1999 |
| DE | 198 20 808 | 11/1999 |
| EP | 0 073 558 | 3/1983 |
| EP | 0 147 168 | 7/1985 |
| EP | 0 617 977 A1 | 2/1994 |
| EP | 0 596 700 | 5/1994 |
| EP | 0 758 451 B1 | 1/1999 |
| EP | 000760723-000 | 7/2007 |
| EP | 2217316 | 7/2010 |
| EP | 2 222 686 | 8/2010 |
| EP | 2 147 003 | 4/2011 |
| EP | 2 054 476 | 6/2011 |
| FR | 2350831 | 12/1977 |
| FR | 2624007 | 6/1989 |
| GB | 1 123 094 | 8/1968 |
| GB | 1 447 163 | 8/1976 |
| GB | 2 048 682 | 12/1980 |
| JP | 53-68249 | 6/1978 |
| JP | 54-13347 | 1/1979 |
| JP | 54-111363 | 8/1979 |
| JP | 54-155856 | 12/1979 |
| JP | 56-116752 | 9/1981 |
| JP | 56-116754 | 9/1981 |
| JP | 0162921 | 9/1983 |
| JP | 3-52936 | 3/1991 |
| JP | 1332866 | 5/2008 |
| JP | 2009-544729 | 12/2009 |
| JP | 2010-507711 | 3/2010 |
| JP | 2010-517693 | 5/2010 |
| JP | 2010-518397 | 5/2010 |
| JP | 2010-526599 | 8/2010 |
| JP | 2010-527010 | 8/2010 |
| JP | 2010-535903 | 11/2010 |
| JP | 2011-504399 | 2/2011 |
| JP | 2011-511755 | 4/2011 |
| SU | 6216724 | 8/1978 |
| WO | WO 87/00920 | 2/1987 |
| WO | WO 88/04415 | 6/1988 |
| WO | WO 92/19150 | 11/1992 |
| WO | WO 96/22798 | 8/1996 |
| WO | WO 97/20530 | 6/1997 |
| WO | WO 97/37713 | 10/1997 |
| WO | WO 97/48437 | 12/1997 |
| WO | WO 98/08554 | 3/1998 |
| WO | WO 00/02048 | 1/2000 |
| WO | WO 00/43536 | 7/2000 |
| WO | WO 02/46752 A2 | 6/2002 |
| WO | WO 03/034047 A | 4/2003 |
| WO | WO 2004/099778 A1 | 11/2004 |
| WO | WO 2005/090014 A1 | 4/2005 |
| WO | WO 2005/065241 A | 7/2005 |
| WO | WO 2006/044973 | 4/2006 |
| WO | WO 2007/067743 A2 | 6/2007 |
| WO | WO 2008/014280 A2 | 1/2008 |
| WO | WO 2008/098011 | 8/2008 |
| WO | WO 2008/098087 | 8/2008 |
| WO | WO 2008/137604 | 11/2008 |
| WO | WO 2008/141241 | 11/2008 |
| WO | WO 2008/141243 | 11/2008 |
| WO | WO 2009/009756 | 1/2009 |
| WO | WO 2009/018426 | 1/2009 |
| WO | WO 2009/021057 | 2/2009 |
| WO | WO 2009/067626 | 5/2009 |
| WO | WO 2009/129186 | 10/2009 |

OTHER PUBLICATIONS

European Examination dated Apr. 1, 2010, re EP Application No. 08 769 266.1-1211.
European Examination Report dated May 11, 2010, re EP Application No. 08 729 209.0.
European Examination Report re App. No. 08 797 302.0, dated Jan. 24, 2011.
European Examination Report re Application No. 08 755 267.5, dated Apr. 26, 2010.
European Examination Report re Application No. 08 755 267.5, dated Sep. 14, 2010.
Furnary A.P. et al. "Effect of hyperglycemia and continuous intravenous insulin infusions on outcomes of cardiac surgical procedures: The Portland Diabetic Project", Endocrine Practice, Mar./Apr. 2004, pp. 21-33, vol. 10.
Hirata O. et al. 2002 "Allosteric saccharide sensing by a phenylboronic-acids-appended 5,15-bis(triarylethynyl)porphyrin" J Supramolecular Chemistry 2:133-142.
Hirsch Irl B. et al. "Acute Complications of Diabetes" Endocrinology and Metabolism Clinics of North America, Dec. 2000, pp. 745-771, vol. 29-4.
Leijten FSS & De Weerdt A W 1994 Critical illness polyneuropathy: a review of the literature, definition and pathophysiology. Clinical Neurology and Neurosurgery, 96: 10-19.
Mizock B A. Am J Med 1995; 98: 75-84.
PCT Partial Search Report re PCT/US2008/053226 dated Jun. 27, 2008.
PCT International Search Report re PCT/US2007/074255 dated Jul. 8, 2008 in 3 pages.
PCT Report on Patentability and Written Opinion re PCT/US2007/074255 dated Jan. 27, 2009 in 9 pages.
PCT International Preliminary Report on Patentability and Written Opinion re PCT/US2008/053097 dated Aug. 11, 2009.
PCT International Preliminary Report and Written Opinion re PCT/US2009/040379 dated Oct. 19, 2010.
PCT International Search Report (Declaration of Non-Establishment of ISR) and Written Opinion re PCT/US2009/040379 dated Aug. 4, 2009.
PCT Report on Patentability and Written Opinion re PCT/US2008/063332 dated Nov. 19, 2009.
PCT International Preliminary Report on Patentabilitu re PCT/US2008/063330 dated Nov. 19, 2009.
PCT International Preliminary Report on Patentability and Written Opinion re PCT/US2008/072359, dated Feb. 9, 2010.
PCT International Search Report and Written Opinion re PCT/US2008/072359 dated Dec. 15, 2008.
PCT Partial International Search Report re PCT/US2008/072359 dated Oct. 15, 2008.
PCT International Search Report and Written Opinion re PCT/US2008/069855 dated Apr. 16, 2009.
PCT Preliminary Report re PCT/US2008/084239 dated May 25, 2010.
PCT International Search Report and Written Opinion re PCT/US2008/084239 dated Jan. 29, 2009.
PCT International Search Report and Written Opinion re PCT/US2010/044761, dated Oct. 6, 2010.
PCT International Search Report and Written Opinion re App. No. PCT/US10/61169, dated Mar. 1, 2011.
PCT International Search Report and Written Opinion re PCT/US2010/037502, dated Aug. 6, 2010.
PCT International Search Report and Written Opinion re PCT App. No. PCT/US 10/50910, dated Dec. 3, 2010.
PCT International Search Report and Written Opinion re App. No. PCT/US 10/61163, dated Mar. 9, 2011.
PCT International Search Report and Written Opinion re App. No. PCT/US10/61173, dated Feb. 28, 2011.
PCT International Search Report and Written Opinion in App. No. PCT/US2011/028222, dated May 6, 2011, in 30 pages.
PCT Search Report and Written Opinion re PCT/US2011/023939, dated Jul. 27, 2011.
PCT International Search Report and Written Opinion re PCT/US2011/034167, mailed Jul. 29, 2011.
University of Santa Cruz, "Optical Glucose Sensor Holds Promise for Diabetics and Intensive Care Patients", Mar. 18, 2004, in 6 pages.
Van Den Berghe G., et al. "Intensive Insulin Therapy in the Medical ICU", The New England Journal of Medicine, Feb. 2, 2006, pp. 449-461, vol. 354-5.
Wilson, Intensive Insulin Therapy in Critical Care, Diabetes Care, Apr. 2007, pp. 1005-1011, vol. 30-4.
Zochodne D W et al. 1987 Polyneuropathy associated with critical illness: a complication of sepsis and multiple organ failure. Brain, 110: 819-842.
Co-pending U.S. Appl. No. 60/833,081, entitled "HPTS-CYS-MA Fluorescent Dye for Use in Glucose Sensing," filed Jul. 25, 2006.

Co-pending U.S. Appl. No. 60/888,477, entitled "Optical Systems and Methods for Ratiometric Measurement of Blood Glucose Concentration," filed Feb. 6, 2007.
PCT Application No. PCT/US2008/063330; Sep. 5, 2008.
PCT Application No. PCT/US2008/063332; Sep. 5, 2008.
International Search Report dated May 27, 2008 for PCT Application No. PCT/US2008/052204, entitled Optical Determination of Ph and Glucose, filed Jan. 28, 2008.
International Search Report, International Application No. PCT/US2008/053097.
International Search Report and Written Opinion Received in PCT/US2008/053226, dated Oct. 15, 2008.
PCT International Search Report for App. No. PCT/US2008/63330 dated Sep. 3, 2008.
Partial International Search Report for PCT Application No. PCT/US2008/063332, entitled Device and Methods for Calibrating Analyte Sensors, filed May 9, 2008.
Agayn, V. I. and Dr. R. Walt (1993). "Fiber-optic sensor for continuous monitoring of fermentation Ph." Biotechnology 72(6):6-9.
Angel, S. M., "Optrodes: Chemically Selective Fiber Optic Sensors," Spectoscopy, Apr. 1987, pp. 38-47.
Badugu, R. et al. "Boronic acid fluorescent sensors for monosaccharide signaling based on the 6-methoxyquinolinium heterocyclic nucleus: progress toward noninvasive and continuous glucose monitoring." 2005 Bioorg. Med. Chem. 13 (1):113-119.
Badugu, R. et al. "Fluorescence sensors for monosaccharides based on the 6-methylquinolinium nucleus and boronic acid moiety: potential application to ophthalmic diagnostics." 2005 *Talanta* 65 (3):762-768.
Badugu, R. et al. "Wavelength-ratio metric near-physiological Ph sensors based on 6-aminoquinolinium boronic acid probes." 2005 *Talanta* 66:569-574.
Bean & Johnson, 54 *J. Am. Chem. Soc.* 4415 (1932).
Burnett, Peebles & Hageman, 96 *Biochemical and Biophysical Research Communications* 157 (1980).
Cappuccio, F. E., et al. 2004 "Evaluation of pyranine derivatives in boronic acid based saccharide sensing: Significance of charge interaction between dye and quencher in solution and hydrogel" *Journal of Fluorescence* 14:521-533.
Cordes, D. B., et al., 2006, in *Topics in Flourescence Spectroscopy*; vol. 11, *Glucose Sensing* Springer "Two component optical sugar sensing using boronic acid-substituted viologens with anionic flourescent dyes" pp. 47-87.
Dawson, et al., 98 *JACS* 5996 (1970).
Definition of "cathether" from Webster's Ninth New Collegiate Dictionary, 1990, p. 216.
English Translation of DE 3,720,736, Jan. 5, 1989.
Forster, "Intermolecular Energy Transfer and Fluorescence, Annaten der Physik" (1948) pp. 55-75.
Gamoh, et al., 222 *Analytica Chimica Acta* 201 (1989).
Gamsey, S., et al., 2006. "Continuous glucose detection using boronic acid-substituted viologens in fluorescent hydrogels: linker effects and extension to fiber optics" *Langmuir* 22:9067-9074.
Gehrich, J. L., D. W. Lubbers, et al. (1986). "Optical fluorescence and its application to an intravascular blood gas monitoring system." IEEE Transactions on Bio-med. Eng., BME-33: 117-132.
Glazer, 59 *Biochemistry* 996 (1968).
Glazer, *Chemical Abstracts*, vol. 68, No. 111805q (1968).
Guilbault, George E., "Practical Fluorescence" (1973), pp. 599-600.
Hakkinen, Lajunen & Purokoski, *A Potentiometric Study on the Complex Formation of Lactitol and Maltitol with Some Inorganic Oxyacids in Aqueous Solution*, Chemical Abstracts, vol. 110, No. 83116f (1989).
Hakkinen, Purokoski & Lajunen, *A Potentiometric Study on the Complex Formation of Germanic Acid and Germanate Ion with Sugar Acids and Disaccharides in Aqueous Solution*, Chemical Abstracts, vol. 105, No. 233265s (1986).
Hayashi, et al., 149 *Clinica Chimica Acta* 149 (1985).
Hirshfeld, "Reabsorption Sensing in Fluorescence Spectroscopy," UCRL Abstract No. 89736 ABST, published by Pittsberg Conference on Scientific Instrumentation, Mar. 1984.

The Immunoassay Handbook, pp. 1-618, ed. David Wild, Macmillan Press, 1994, United Kingdom.
Kirk-Othmer, Encyclopedia of Chemical Technology, $3^{rd}$ ed., vol. 8, John Wiley and Sons, New York, pp. 201-203 (1979).
Kostov, Y., P. Harms, et al. (2001). "Low-cost microbioreactor for high-throughput bioprocessing." Biotechnol Bioeng 72: 346-352.
Lakowitz, et al., Analytica Chimica Acta, 271, (1993), 155-164.
Lindner, et al., 473 *J. Chromatography* 227-240 (1989).
Lutty, G.A. (1978). "The acute intravenous toxicity of stains, dyes, and other fluorescent substances." Toxicol Pharmacol. 44: 225-229.
Meadows and Schultz (1993) Anal. Chim. Acta 280: pp. 21-30.
Medtronic, Features of the Guardian REAL-Time Continuous Glucose Monitoring System, Features that fit your diabetes management lifestyle, located at http://www.minimed.com/products/guardian/features.html on Aug. 28, 2007.
Mosbach, *Methods in Enzymology*, vol. XLIV, 53 (1976).
Niu, C. G. et al. "Fluorescence ratiometric Ph sensor prepared from covalently immobilized porphyrin and benzothioxanthene." 2005 *Anal. Bioanal. Chem.* 383(2):349-357.
Offenbacher, H., O. S. Wolfbeis, et al. (1986). "Fluorescence optical sensors for continuous determination of near-neutral Ph values." Sensor Actuator 9: 73-84.
Purokoski, Lajunen & Hakkinen, *A Potentiometric Study on the Complex Formation of Arsenious Acid, Arsenite Ion, Telluric Acid and Tellurate Ion with Sugar Acids and Disaccharides in Aqueous Solution*, Chemical Abstracts, vol. 107, No. 122178n (1987).
Roy, et al., *J. Inorg. Nucl. Chem.*, 106 (1957).
Schulman, S. G., S. Chen, et al. (1995). "Dependence of the fluorescence of immobilized 1-hydroxypyrene-3,6,8-trisulfonate on solution pH: extension of the range of applicability of a pH fluorosensor." Anal Chim Acta 304: 165-170.
Seitz, "Chemical Sensors Based on Fiber Optics," Analytical Chemistry, vol. 56, pp. 16a-34a, 1984.
Sharrett, Z., et al. 2008 "Boronic acid-appended bis-viologens as a new family of viologen quenchers for glucose sensing" *Tetrahedron Letters* 49:300-304.
Snyder, et al., "The Preparation of Some Azo Boronic Acids," 70 *J. Am. Chem. Soc.* 232 (1948).
Song, A., S. Parus, et al. (1997) "High-performance fiber-optic pH microsensors for practical physiological measurements using a dual-emission sensitive dye." Analytical Chemistry 69: 863-867.
Streitwieser, Jr. & Heathcock, *Introduction to Organic Chemistry* (1976).
Sturdevant, M. F., "How Sterilization Changes Long-Term Resin Properties," Plastics Engineering, Jan. 1991, pp. 27-32.
Suri, J. T., et al. 2003 "Continuous glucose sensing with a fluorescent thin-film hydrogel" *Angew Chem Int Ed* 42:5857-5859.
Turner, N. G. et al. "Determination of the pH Gradient Across the Stratum Corneum." *1998 J. Investig. Dermatol. Symp. Proc.* Aug. 3(2):110-3.
Udenfreund, "Fluorescence Assay in Biology and Medicine" (1962) pp. 108-109.
Van Kempien & Kreuzer, "A Single-Unit Carbon Dioxide Sensing Microelectrode System," Respiration Physiology, (1975), 23, 371-379.
Vermeer, et al., 37 *Tetr. Letters* 3255 (1970).
Wolfbeis, O. S., E. Fuerlinger, et al. (1983). "Fluorimetric analysis. I. Study on fluorescent indicators for measuring near neutral ('physiological') pH values." Fresneius' Z. Anal. Chem. 314 (2): 119124.
Xu, Z., A. Rollins, et al. (1998) "A novel fiber-optic pH sensor incorporating carboxy SNAFL-2 and fluorescent wavelength-ratiometric detection" Journal of Biomedical Materials Research 39:9-15.
Zhang, S., S. Tanaka, et al. (1995). "Fibre-optical sensor based on fluorescent indicator for monitoring physiological pH values." Med Biol Eng Comput 33: 152-156.
Zhujun, Z. and W. R. Seitz (1984). "A fluorescence sensor for quantifying pH in the range from 6.5 to 8.5." Analytical Chimica Acta 160:47-55.
Zhujun, Z., et al, (1984). Analytical Chimica Acta 160:305-309.

* cited by examiner

SENSOR FOR PERCUTANEOUS INTRAVASCULAR DEPLOYMENT WITHOUT AN INDWELLING CANNULA

CROSS-REFERENCE TO RELATED APPLICATIONS

This application claims the benefit of U.S. Provisional Patent Application No. 61/045,887, filed Apr. 17, 2008, the entire contents of which are incorporated herein by reference and should be considered a part of this specification.

BACKGROUND OF THE INVENTION

1. Field of the Invention

A sensor for intravascular residence is disclosed along with methods for percutaneous deployment of the sensor. In preferred embodiments, the sensor is a fiber-optic glucose sensor which is inserted and resides in a peripheral vein without an indwelling cannula.

2. Description of the Related Art

Despite advances in glucose detection technologies, there are no minimally invasive, accurate, real-time, in vivo sensors on the market for monitoring glucose levels over a period of days or weeks. Consequently, it has been a significant burden on diabetics, patients and hospital staff to perform frequent blood sampling for conventional ex vivo blood glucose monitoring. There are short-term continuous glucose sensors that use enzyme-based glucose detection in the interstitial fluid. However, such sensors are relatively large, complex and expensive. These electrochemical sensors also consume reactants (e.g., glucose), which may become limiting particularly when the sensors are walled off due to the patient's foreign body reaction. Moreover, the equilibration lag time may change and the correlation between blood and interstitial glucose levels may become tenuous, particularly in seriously ill (e.g., ICU) patients.

Intravascular sensor deployment raises other technical difficulties. Typically, one sensor for each analyte has been placed in a patient's blood vessel(s) through an indwelling cannula. If it is desired to measure several analytes, a plurality of sensors are often required, which can cause attendant discomfort to the patient and complexity of the electronic monitoring equipment. Moreover, even the deployment of a single sensor within a peripheral vein presents continuous maintenance issues for the nursing staff. The present state of the art is that sensors are deployed through indwelling cannulas. Because blood becomes trapped and clots within such cannulas and between the cannula and the sensor, the cannula must be flushed continuously or periodically, typically with saline/heparin. In the ICU, for example, the nursing staff regularly purge (e.g., every 4 hrs) the trapped blood and clots, to maintain cannula access to the vein open.

Accordingly, there remains an important unmet need for a sensor configured for intravascular deployment and methods of deploying such a sensor, wherein the sensor by itself is left to reside within the vein, without any additional structural components (e.g., an indwelling cannula).

SUMMARY OF THE INVENTION

A method is disclosed for deploying a sensor in a blood vessel of a patient. The method comprises positioning the sensor in the blood vessel, such that at least a distal portion of the sensor resides within the blood vessel and at least a proximal portion of the sensor extends out of the patient, wherein there are no additional components associated with the sensor within the patient.

In one preferred embodiment, the blood vessel is a peripheral vein. In another preferred embodiment, the sensor is an optical fiber glucose sensor.

In one embodiment, the step of positioning the sensor further comprises introducing the sensor into the blood vessel through an introducer assembly.

In another embodiment, the step of positioning the sensor further comprises removing the introducer assembly, leaving only the sensor in the patient.

A method for measuring an analyte concentration in a blood vessel is disclosed in accordance with another embodiment. The method comprises: providing a sensor configured to reside at least in part within the blood vessel and generate a signal related to the analyte concentration in the blood; introducing the sensor into the blood vessel through an introducer assembly; removing the introducer assembly, leaving only the analyte sensor in the patient; and detecting the signal to measure the analyte concentration in the blood.

A method for deploying a sensor in a blood vessel is disclosed in accordance with another embodiment. The method comprises: providing an introducer assembly comprising a hypodermic needle slidably engaged within a splitable cannula, wherein a piercing tip of the hypodermic needle extends distally beyond the splitable cannula; cannulating the blood vessel with the introducer assembly; withdrawing the hypodermic needle, leaving the splitable cannula in the vessel; inserting the sensor through the splitable cannula and into the vessel; withdrawing the splitable cannula from the vessel, leaving the sensor in the vessel; and splitting and removing the cannula from the sensor.

A method for continuous monitoring of blood glucose levels in a patient is disclosed in accordance with another embodiment. The method comprises: providing an introducer assembly comprising a hypodermic needle slidably engaged within a removable cannula, wherein a piercing tip of the hypodermic needle extends distally beyond the removable cannula; inserting the introducer assembly into a peripheral vein; retracting the hypodermic needle from the removable cannula, while leaving the removable cannula in the peripheral vein; providing an optical glucose sensor comprising a fluorescent indicator system disposed along a distal end region and adapted to generate an optical signal related to the blood glucose level in response to light, an elongate fiber-optic body, and an optical coupling disposed along a proximal end region; inserting the optical glucose sensor through the removable cannula and into the peripheral vein; retracting the removable cannula from the vein, while leaving the sensor in the peripheral vein; removing the removable cannula from the sensor; connecting the optical coupling to a device comprising a light source and a detector; and detecting the optical signal to monitor the blood glucose level of the patient. In one preferred embodiment, the removable cannula has at least one scoring such that the removable cannula can be split.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of

DETAILED DESCRIPTION OF THE PREFERRED EMBODIMENT

In one embodiment, the present invention involves a method for deploying a sensor in a blood vessel of a patient, wherein the sensor resides within the patient without any additional device or structural components, e.g., introducer, cannula, catheter, sleeve, etc. The deployment of a naked, preferably very small and non-thrombogenic, sensor addresses some of the disadvantages that presently face patients and medical staff, e.g., thrombogenesis, constant staff care, etc. The sensor can be adapted to sense any analyte using known sensing systems and/or chemistries. The blood vessel can be an artery or a vein. The method comprises positioning the sensor in the blood vessel, such that a distal portion of the sensor resides within the blood vessel by itself, and a proximal portion of the sensor extends out of the patient, wherein there are no additional components associated with the sensor within the patient.

More particularly, new and elegant solutions to some of the technical challenges faced by patients and medical staff in using existing in vivo glucose sensors are disclosed. In one embodiment, a solution to the technical challenges involves using a sensor comprising equilibrium, non-consuming fluorescence-based detection chemistry. Equilibrium optical sensing addresses the problems associated with rate-limiting consumption of enzymatic reactants in current electrochemical sensors. Further, placement within a peripheral vein, as opposed to subcutaneous (interstitial) placement, provides direct monitoring of blood glucose levels, thereby avoiding the problems associated with measuring glucose levels in the interstitial fluid-e.g., uncertain and changing equilibration time for glucose between the blood and the interstitial fluid. In another embodiment, deployment of a very small diameter, non-thrombogenic fiber-optic sensor within a vein, without an indwelling cannula, addresses the serious burden on the nursing staff related to continuous or periodic flushing of the cannula to maintain open access to the vein.

Examples of small diameter, equilibrium optical sensors are disclosed in U.S. Pat. No. 6,627,177 and U.S. Patent Publ. No. 2006/0083688, and co-pending U.S. patent application Ser. Nos. 11/296,898; 11/782,553; 11/671,880; 12/027,158; 12/026,396; 60/917,309; 60/917,307; 60/954,204; 60/915,372; 60/949,145; and 60/989,732; each of which is incorporated herein in its entirety by reference thereto.

Processes for inserting catheters into a blood vessel are known. Generally, a hypodermic needle is first inserted into the blood vessel. Once the hypodermic needle is in place in the blood vessel, a guidewire may be threaded through the hypodermic needle and into the blood vessel. After the guidewire has been inserted into the blood vessel through the hypodermic needle, the hypodermic needle can be removed, leaving the guidewire in place in the blood vessel. Next, a cannula is threaded over the guidewire and into the blood vessel. Finally, the guidewire is removed and the catheter is introduced into the blood vessel through the cannula. When the catheter is an analyte sensor, the cannula is left indwelling.

In preferred embodiments, the present invention relates to a fiber-optic glucose sensor that is introduced into and resides within a blood vessel (or interstitial site) by itself, without an indwelling cannula or permanent introducer. The small diameter and flexibility of such a sensor provide obvious advantages in relation to patient comfort. Liao, K.-C., et al., Biosens. Bioelectron. (2008), doi: 10.1016/j.bios.2008.01.012 recently disclosed a smaller and less invasive glucose sensor designed for interstitial implantation, wherein glucose sensitivity is mediated by Con A binding and Quantum dots are used as FRET donors; the sensor chemistry is immobilized at the end of an optical fiber in a PEG-DA hydrogel. However, Liao et al., does not disclose intravascular deployment. Interstitial fluid is generally slow to equilibrate with glucose. Thus, intravascular monitoring is highly preferred because it is the glucose in blood that is important, particularly where patients are critically ill and the medical staff is trying to maintain tight glycemic control. Very sick patients tend to exhibit huge fluid shifts, which dramatically change glucose response time/correlation between blood glucose and interstitial fluid glucose.

In some embodiments, e.g., for walking diabetics, interstitial deployment of an equilibrium fiber-optic sensor may be utilized. The equilibrium between blood and interstitial fluid glucose will tend to be relatively constant in such patients, wherein the convenience (less-invasive nature) of interstitial deployment may be preferred.

Figure 1:
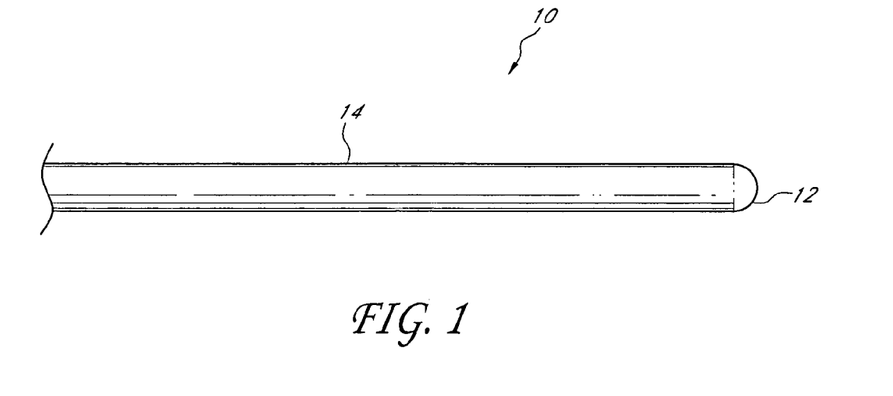
FIG. 1 shows a side view of an embodiment of an intravascular sensor.

FIG. 1 shows an embodiment of a sensor 10 having a distal end 12 and an elongate body 14 that can be percutaneously inserted into a blood vessel, such as a vein or artery, for intravascular residence. In some embodiments, the vein or artery can be a peripheral vein or a peripheral artery, while in other embodiments, the vein or artery can be a central vein or a central artery. In some embodiments, the sensor can be interstitially deployed. The sensor 10 can be a sensor for measuring any compound, metabolite, chemical, protein, molecule, nutrient, and/or hemodynamic parameter of interest. For example, the sensor 10 can be a sensor for measuring glucose, ions such as potassium, blood gases, such as oxygen and carbon dioxide, flow rate, pressure, pH, or any other measurable analyte. In some embodiments, as illustrated in FIG. 1, the sensor 10 is a fiber-optic glucose sensor as further described in co-pending U.S. application Ser. No. 12/026, 396, filed Feb. 5, 2008 and U.S. application Ser. No. 12/027, 158, filed Feb. 6, 2008, both of which are incorporated herein by reference in their entireties.

Figure 2:
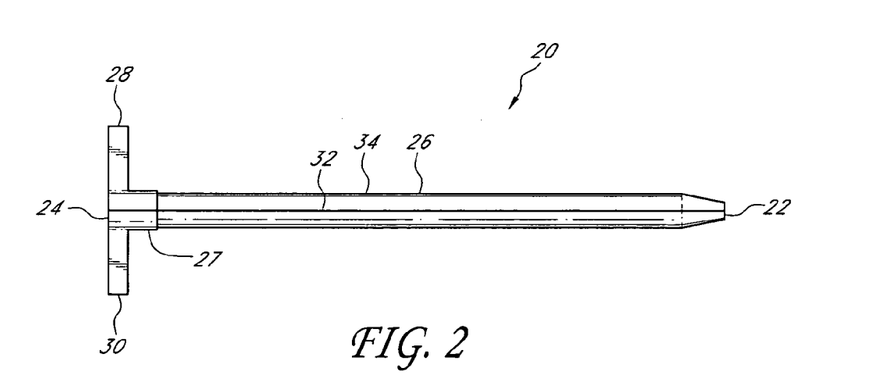
FIG. 2 shows a side view of one embodiment of a peelable introducer.
Figure 3:
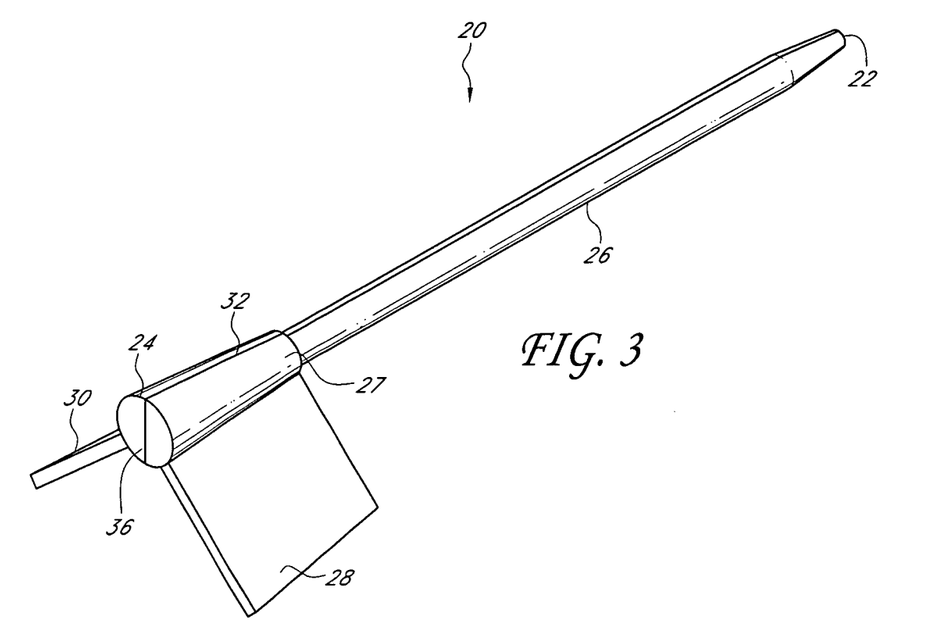
FIG. 3 shows a perspective view of one embodiment of a splitable introducer.
Figure 4A:
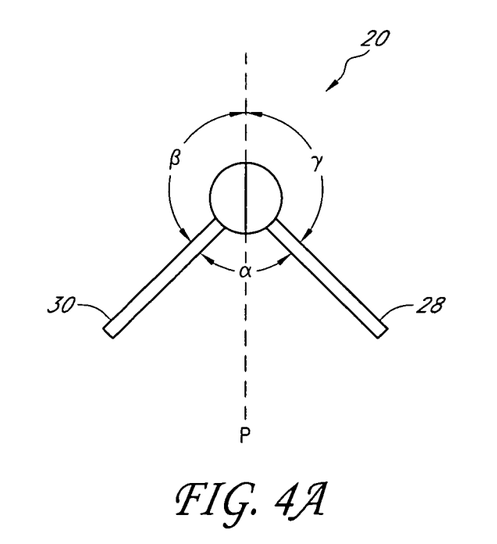
FIG. 4A shows a back view of the splitable introducer of FIG. 3.
Figure 4B:
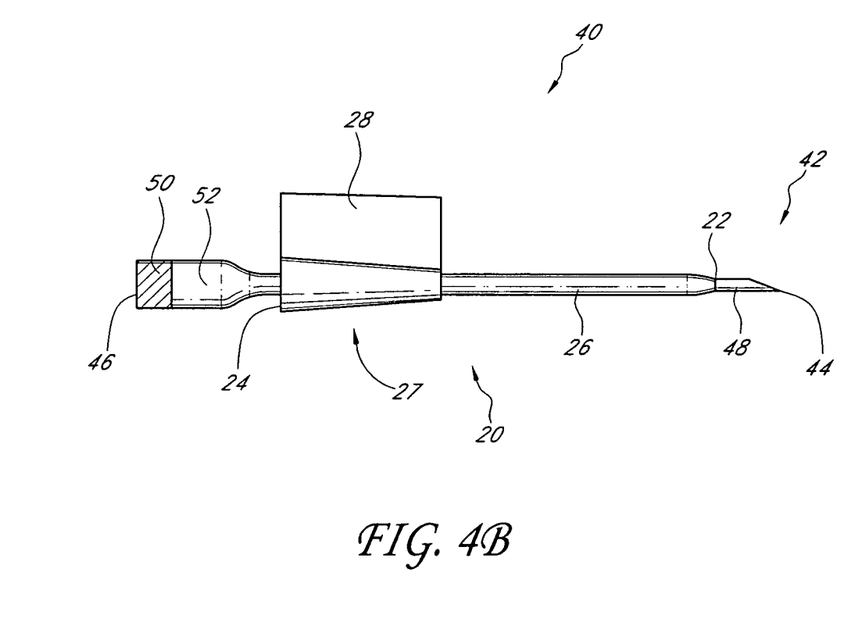
FIG. 4B shows a side view of an introducer assembly comprising the splitable introducer of FIG. 3 and a hypodermic needle.

The sensor 10 can be percutaneously introduced into a blood vessel by using a removable introducer 20, embodiments of which are illustrated in FIGS. 2-4. The introducer 20 can be, for example, peelable or splitable. One embodiment of a peelable introducer 20 is shown in FIG. 2. The introducer 20 has a distal end 22, a proximal end 24 and an elongate body 26 having a lumen therebetween. In some embodiments, the elongate body 26 can be a sheath or tubular structure with thin walls. The proximal end 24 comprises a hub 27 having a first wing 28 and a second wing 30 that extend transversely away from the elongate body 26. The first wing 28 and second wing 30 are located opposite or substantially opposite each other. The elongate body 26 can have two longitudinal score lines 32, 34 which are located opposite or substantially opposite each other and divide the elongate body 26 into two halves, each half attached to a wing. The score lines 32, 34 are weakened portions of the elongate body 26 that allow the introducer 20 to be split in half by grasping the wings 28, 30 and pulling the wings 28, 30 apart.

FIGS. 3 and 4A and 4B illustrate an embodiment of a splitable introducer 20. As shown in FIG. 3, the splitable introducer 20 has a distal end 22, a proximal end 24 and an elongate body 26 having a lumen 36 therebetween. The proximal end 24 comprises a hub 27 having a first wing 28 and a second wing 30 that extend transversely away from the elongate body 26. As shown in FIG. 4A, the first wing 28 and the second wing 30 can be attached to the hub 27 at an angle α to each other. In some embodiments, the angle α between the first wing 28 and the second wing 30 is less than about 120 degrees.

As shown in FIG. 3, the splitable introducer 20 has a single score line 32 that runs along the length of the elongate body 26 and hub 27. The score line 32 is located on a portion of the splitable introducer 20 that generally opposes the first wing 28 and the second wing 30. For example, as shown in FIG. 4A, the splitable introducer 20 can be divided in half longitudinally by plane P which also bisects angle α. The score line 32 is located at an angle γ from the first wing 28 and at an angle β from the second wing. In some embodiments, β and γ are approximately equal. In some embodiments, β and γ are at least about 120 degrees. The splitable introducer 20 can be split along the score line 32 by squeezing the first wing 28 and the second wing 30 together. In some embodiments, squeezing can advantageously be accomplished by using just one hand.

FIG. 4B illustrates an introducer assembly 40 comprising a splitable introducer 20 and a hypodermic needle 42 disposed therein. The hypodermic needle 42 has a distal end 44 and a proximal end 46 and a cannula 48 extending therebetween. The distal end 44 of the cannula 48 can be beveled to terminate in a sharp point that facilitates entry of the hypodermic needle 42 into the patient's tissue. The proximal portion of the hypodermic needle can include a filter 50 and flashback chamber 52. When the distal end 44 of the hypodermic need 42 is inserted into a blood vessel or interstitial space, blood or interstitial fluid will fill the flashback chamber 52, thereby facilitating the correct placement of the introducer assembly 40 into the blood vessel. The filter 50 can function to contain the blood within the flashback chamber 52 and to reduce the likelihood of contamination of the blood, thereby reducing the chance of infection. As illustrated, the cannula 48 is removably disposed within the lumen 36 of the elongate body 26 of the splitable introducer 20. After the introducer assembly 40 is inserted in the blood vessel or interstitial space, the hypodermic needle 42 can be withdrawn from the splitable introducer 20, leaving just the splitable introducer 20 in the blood vessel or interstitial space.

Additional types of removable introducers 20 are also suitable for introducing the sensor 10 into a blood vessel. For example, an introducer 20 that can be removed by cutting can be used in some embodiments. The cutting tool used to cut the introducer 20 can be designed to cut the introducer 20 without damaging the sensor 10 underneath.

In some embodiments, the introducer 20 can be made out of a metal, metal alloy, resin (for example, a thermosetting resin such as an epoxy resin or phenolic resin), polymer (for example, a thermoplastic polymer or, in some cases, an elastomeric polymer) or a combination of the forgoing compounds. The polymer can be polyacrylate, polyurethane, polysulfone, polypropylene, polytetrafluoroethylene, polyethylene, polystyrene, polymethyl methacrylate, polycarbonate, polyethylene terephthalate, polyvinyl chloride, or any other suitable polymer. In certain embodiments, the introducer comprises polyurethane.

Examples of removable introducers that can be used in accordance with some embodiments are described in U.S. Pat. Nos. 4,345,606, 5,141,497, 5,334,157, 5,409,469, 6,273,874, and 6,663,595, and EP 0402057B1; each of which is incorporated in its entirety by reference thereto.

In some embodiments, an introducer assembly comprises an introducer with a hypodermic needle coaxially engaged within the lumen of the introducer. The hypodermic needle or stylus is typically within the lumen of the introducer 20 before the introducer 20 is inserted into the patient to access the patient's blood vessel or interstitial site. The distal end of the hypodermic needle or stylus can extend beyond the distal end 22 of the introducer 20 so that the hypodermic needle or stylus can help the introducer 20 penetrate the patient's tissue to access the blood vessel. In addition, the hypodermic needle can help the medical practitioner locate the blood vessel by allowing the medical practitioner to visualize blood when the hypodermic needle enters a blood vessel. It is understood that any member capable of piercing the skin and traversing the underlying tissue can be used in accordance with embodiments of the invention—it need not be a "hypodermic needle" per se. In one embodiment, the introducer itself may comprise a beveled or otherwise piercing distal end that is splitable, peelable, etc., such that a separate needle need not be used to access the blood vessel or interstitial site.

In some embodiments, the hypodermic needle has a diameter that is only slightly less than the diameter of the elongate body 26 of the introducer 20. This can be accomplished by making the walls of the elongate body 26 relatively thin. In addition, the hypodermic needle can have a diameter that is only slightly less than the lumen 36 of the introducer 20 so that the hypodermic needle fits snugly into the lumen 36. In some embodiments, the distal end 22 of the introducer 20 can be beveled or tapered to provide a gradual increase in diameter of the distal portion of the elongate body 26. In some embodiments, e.g., where a metal needle and a stretchable polymeric introducer are employed, the diameter of the needle may be equal to or even larger than the diameter of the introducer, such that the introducer expands to accommodate the needle.

The hypodermic needle, which projects past the distal end 22 of the introducer 20, is used to puncture the skin and tissue of the patient, creating a hole with a diameter substantially equal to the diameter of the hypodermic needle. As the hypodermic needle and introducer 20 are advanced through the patient's tissue and into the blood vessel or interstitial site, the distal end 22 of the introducer 20 enters the hole made by the hypodermic needle. As described above, in some embodiments the beveled or tapered distal end 22 facilitates insertion of the elongate body 26 of the introducer 20 into the hole made by the hypodermic needle by closely matching the diameter of the distal end 22 to the diameter of the hole. The beveled or tapered distal end 22 also allows the hole to be gradually stretched wider, rather than further cutting or tearing the tissue, as the introducer is advanced. The wall of the elongate body 26 can be thin in order to reduce the degree of widening of the hole that occurs as the introducer is advanced. In addition, the gradual widening or stretching of the hole facilitates the formation of a tight seal between the patient's tissue and the elongate body 26.

After the introducer 20 is inserted into the blood vessel, the hypodermic needle or stylus can be removed from the lumen 36 of the introducer 20. In some embodiments, the elongate body 26 can be flexible and kink resistant. The elongate body 26 can be made flexible by fabricating the elongate body 26 out of a polymer such as polyacrylate, polyurethane, polysulfone, polypropylene, polytetrafluoroethylene, polyethylene, polystyrene, polymethyl methacrylate, polycarbonate, polyethylene terephthalate, polyvinyl chloride, or any other suitable polymer. The elongate body 26 can be made stiff, while maintaining its flexibility, and kink resistant by embedding or incorporating a coil of wire into the polymer elongate body 26. This is especially true for elastomeric polymers, such as polyacrylate and polyurethane. Preferably, the wire is very thin and can be made out of a variety of metals or metal alloys, such as steel, nickel, titanium, aluminum or a combination of each. However, in some embodiments, the elongate body 26 does not comprise a coil of wire. Making the elongate body 26 flexible and kink resistant reduces the likelihood that the lumen 36 will kink or collapse, which can make insertion of the sensor 10 through the introducer 20 difficult.

The sensor 10, a fiber-optic glucose sensor in preferred embodiments, can be inserted into the lumen 36 of the introducer 20 and into the blood vessel. In some embodiments, the sensor 10 has a diameter that is the same as or substantially similar to the diameter of the hypodermic needle or to the inner diameter of the lumen 36 of the introducer 20. The sensor 10 can have a smooth surface to facilitate passage of the sensor 10 through the lumen 36 of the introducer 20. In some embodiments, a lubricant can be used to facilitate passage of the sensor 10 through the lumen 36 of the introducer 20.

After the sensor 10 has been introduced into the blood vessel or interstitial site through the lumen 36 of the introducer 20, the introducer 20 can be withdrawn from the patient's tissue. The introducer 20 can be removed from the sensor 10 by peeling, splitting or cutting the introducer 20, as described above.

Once the introducer 20 has been removed, the stretched hole closes around the sensor 10, forming a seal. The surface of the sensor 10 can be made smooth to enhance the seal between the patient's tissue and the surface of the sensor 10. This allows the sensor 10 to reside in the blood vessel or interstitial site without using a permanent indwelling cannula that also resides in the blood vessel or interstitial site.

In some embodiments, the sensor 10 can be given anti-thrombogenic properties by, for example, coating or treating the surface of the sensor 10 with heparin or another compound with anti-thrombogenic properties. In addition, the sensor 10 can be fabricated with a smooth surface having low thrombogenicity. For example, the sensor 10 surface can be made of a polymer such as polytetrafluoroethylene. Portions of the sensor 10 that include a porous or semipermeable membrane can be given a smooth surface by the polymerization of a polymer, such as a hydrogel, within the pores of the membrane, as described in co-pending U.S. application Ser. No. 12/026,396, filed Feb. 5, 2008, which is hereby incorporated by reference in its entirety.

EXAMPLES

In some embodiments, a fiber-optic glucose sensor can be inserted into a blood vessel or an interstitial space of the patient as described herein. The glucose sensor comprises an optical glucose measurement system that measures glucose concentration levels using glucose-sensing chemical indicator systems. Such indicator systems preferably comprise a fluorophore operably coupled to a glucose binding moiety. Preferably, the glucose binding moiety acts as a quencher with respect to the fluorophore (e.g., suppresses the fluorescent emission signal of the fluorophore in response to excitation light when it associates with the fluorophore). In preferred embodiments, as the glucose binding moiety binds glucose (e.g., as glucose concentrations rise), it dissociates from the fluorophore, which then generates a fluorescent emission signal upon excitation. Accordingly, in such embodiments, the higher the glucose concentration, the more glucose bound by the binding moiety, the less quenching, and the higher the fluorescence intensity of the fluorophore upon excitation.

The optical glucose measurement system measures, in certain embodiments, the glucose concentrations intravascularly or interstitially and in real-time through the use of such fluorophore-quencher indicator systems. The glucose-sensing indicator systems can be immobilized in a hydrogel. The hydrogel can be inserted into an optical fiber such that light may be transmitted through the hydrogel while at least a portion of the hydrogel is in contact with blood. The hydrogel is preferably permeable to analytes, specifically glucose. The optical fiber together with the hydrogels can comprise a glucose sensor that is placed in a mammalian (human or animal) blood vessel or interstitial space. In certain embodiments, light is transmitted into the glucose sensor from a light source. The light source can be a light emitting diode that emits an optical excitation signal. The optical excitation signal can excite the fluorophore systems in the presence of glucose, such that the fluorophores emit light at an emission wavelength. In certain embodiments, the fluorophore systems can be configured to emit an optical emission signal at a first wavelength having an intensity related to the blood glucose concentration in the blood vessel or the interstitial fluid glucose concentration in the interstitial space. The light can be directed out of the glucose sensor such that the light is detected by a light sensitive module (or detector system) that can comprise at least one detector. Detectors include any component capable of converting light into a measurable signal, and may include but are not limited to photomultipliers, photodiodes, diode arrays, or the like. The at least one detector can be configured to measure the intensity of the emission wavelength because the intensity of the emission wavelength, in certain embodiments, is related to the glucose concentration present in the blood. In certain embodiments, the light sensitive module (or detector system) comprises an interference filter, an amplifier, and/or an analog-to-digital converter. The light sensitive module (or detector system) can also comprise a microspectrometer, spectrometer, or the like.

Various non-glucose related factors can affect the measurements of the intensity of the emission wavelength, resulting in measurement errors. In certain embodiments, the measurement errors are eliminated or are substantially eliminated or reduced by employing a ratio of certain signals. The measurement errors that may be eliminated include but are not limited to changes in the intensity of the light generated from the light source(s), changes in the coupling efficiency of light into the optical fibers, bending of the optical fiber and the ensuing loss of light from the fiber, changes in the sensitivity of the detection circuit due to, for example, temperature or age or duration of use. In certain embodiments, the ratio of certain signals is unaffected by changes in the light source intensity, the coupling efficiency of the light source into the optical fibers, bending of the optical fibers or the like. The ratio of certain signals can be the ratio of an emission signal to an excitation signal. In certain embodiments, the ratio of certain signals is the ratio of an emission signal to a second optical signal. The second signal may be the excitation light signal which is transmitted through the optical system, through the sensor and indicator system, and reflects back at least in part from the sensor into the light sensitive module (or detector system). Alternatively, the second signal may be generated by a separate reference light, for example red light, which is not absorbed by the indictor system. The second signal may be generated by certain fluorophores as a second emission signal at a different wavelength—the intensity of which is independent of glucose. Any light that is propagated through the optical system, can be either not altered by the glucose concentration or is the excitation light. Light not altered by the glucose concentration can be detected by the light sensitive system (or detector system) and may be used as the second or reference light signal.

From the disclosure herein, it will be apparent to those of ordinary skill in the art that other sources of measurement errors may also be eliminated by employing a ratio of certain signals.

The indicator system (also referred to herein as a fluorophore system) can comprise a fluorophore operably coupled to a quencher. In certain embodiments, the fluorophore system comprises a polymer matrix comprising a fluorophore susceptible to quenching by a viologen, a viologen quencher with quenching efficacy dependent on glucose concentration, and a glucose permeable polymer, wherein said matrix is in contact with blood in vivo. Preferably the fluorophore is a fluorescent organic dye, the quencher is a boronic acid functionalized viologen, and the matrix is a hydrogel.

"Fluorophore" refers to a substance that when illuminated by light at a particular wavelength emits light at a longer wavelength; i.e. it fluoresces. Fluorophores include but are not limited to organic dyes, organometallic compounds, metal chelates, fluorescent conjugated polymers, quantum dots or nanoparticles and combinations of the above. Fluorophores may be discrete moieties or substituents attached to a polymer.

Fluorophores that may be used in preferred embodiments are capable of being excited by light of wavelength at or greater than about 400 nm, with a Stokes shift large enough that the excitation and emission wavelengths are separable by at least 10 nm. In some embodiments, the separation between the excitation and emission wavelengths may be equal to or greater than about 30 nm. These fluorophores are preferably susceptible to quenching by electron acceptor molecules, such as viologens, and are resistant to photo-bleaching. They are also preferably stable against photo-oxidation, hydrolysis and biodegradation.

In some embodiments, the fluorophore may be a discrete compound.

In some embodiments, the fluorophore may be a pendant group or a chain unit in a water-soluble or water-dispersible polymer having molecular weight of about 10,000 daltons or greater, forming a dye-polymer unit. In one embodiment, such dye-polymer unit may also be non-covalently associated with a water-insoluble polymer matrix $M^1$ and is physically immobilized within the polymer matrix $M^1$, wherein $M^1$ is permeable to or in contact with an analyte solution. In another embodiment, the dye on the dye-polymer unit may be negatively charged, and the dye-polymer unit may be immobilized as a complex with a cationic water-soluble polymer, wherein said complex is permeable to or in contact with the analyte solution. In one embodiment, the dye may be one of the polymeric derivatives of hydroxypyrene trisulfonic acid. The polymeric dyes may be water-soluble, water-swellable or dispersible in water. In some embodiments, the polymeric dyes may also be cross-linked. In preferred embodiments, the dye has a negative charge.

In other embodiments, the dye molecule may be covalently bonded to the water-insoluble polymer matrix $M^1$, wherein said $M^1$ is permeable to or in contact with the analyte solution. The dye molecule bonded to $M^1$ may form a structure $M^1$-$L^1$-Dye. $L^1$ is a hydrolytically stable covalent linker that covalently connects the sensing moiety to the polymer or matrix. Examples of $L^1$ include lower alkylene (e.g., $C_1$-$C_8$ alkylene), optionally terminated with or interrupted by one or more divalent connecting groups selected from sulfonamide (—$SO_2NH$—), amide —(C=O)N—, ester —(C=O)—O—, ether.-O—, sulfide —S—, sulfone (—$SO_2$—), phenylene —$C_6H_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like, or a combination thereof. In one embodiment, the dye is bonded to a polymer matrix through the sulfonamide functional groups.

In accordance with broad aspects of the present invention, the analyte binding moiety provides the at least dual functionality of being able to bind analyte and being able to modulate the apparent concentration of the fluorophore (e.g., detected as a change in emission signal intensity) in a manner related to the amount of analyte binding. In preferred embodiments, the analyte binding moiety is associated with a quencher. "Quencher" refers to a compound that reduces the emission of a fluorophore when in its presence. Quencher (Q) is selected from a discrete compound, a reactive intermediate which is convertible to a second discrete compound or to a polymerizable compound or Q is a pendant group or chain unit in a polymer prepared from said reactive intermediate or polymerizable compound, which polymer is water-soluble or dispersible or is an insoluble polymer, said polymer is optionally crosslinked.

In one example, the moiety that provides glucose recognition in the embodiments is an aromatic boronic acid. The boronic acid is covalently bonded to a conjugated nitrogen-containing heterocyclic aromatic bis-onium structure (e.g., a viologen). "Viologen" refers generally to compounds having the basic structure of a nitrogen containing conjugated N-substituted heterocyclic aromatic bis-onium salt, such as 2,2'-, 3,3'- or 4,4'-N,N' bis-(benzyl) bipyridium dihalide (i.e., dichloride, bromide chloride), etc. Viologen also includes the substituted phenanthroline compounds. The boronic acid substituted quencher preferably has a pKa of between about 4 and 9, and reacts reversibly with glucose in aqueous media at a pH from about 6.8 to 7.8 to form boronate esters. The extent of reaction is related to glucose concentration in the medium. Formation of a boronate ester diminishes quenching of the fluorphore by the viologen resulting in an increase in fluorescence dependent on glucose concentration. A useful bis-onium salt is compatible with the analyte solution and capable of producing a detectable change in the fluorescent emission of the dye in the presence of the analyte to be detected.

Bis-onium salts in the embodiments of this invention are prepared from conjugated heterocyclic aromatic di-nitrogen compounds. The conjugated heterocyclic aromatic di-nitrogen compounds are selected from dipyridyls, dipyridyl ethylenes, dipyridyl phenylenes, phenanthrolines, and diazafluorenes, wherein the nitrogen atoms are in a different aromatic ring and are able to form an onium salt. It is understood that all isomers of said conjugated heterocyclic aromatic di-nitrogen compounds in which both nitrogens can be substituted are useful in this invention. In one embodiment, the quencher may be one of the bis-onium salts derived from 3,3'-dipyridyl, 4,4'-dipyridyl and 4,7-phenanthroline.

In some embodiments, the viologen-boronic acid adduct may be a discrete compound having a molecular weight of about 400 daltons or greater. In other embodiments, it may also be a pendant group or a chain unit of a water-soluble or water-dispersible polymer with a molecular weight greater than about 10,000 daltons. In one embodiment, the quencher-polymer unit may be non-covalently associated with a polymer matrix and is physically immobilized therein. In yet another embodiment, the quencher-polymer unit may be immobilized as a complex with a negatively charge water-soluble polymer.

In other embodiments, the viologen-boronic acid moiety may be a pendant group or a chain unit in a crosslinked, hydrophilic polymer or hydrogel sufficiently permeable to the analyte (e.g., glucose) to allow equilibrium to be established.

In other embodiments, the quencher may be covalently bonded to a second water-insoluble polymer matrix $M^2$, which can be represented by the structure $M^2$-$L^2$-Q. $L^2$ is a linker selected from the group consisting of a lower alkylene (e.g., $C_1$-$C_8$ alkylene), sulfonamide, amide, quaternary ammonium, pyridinium, ester, ether, sulfide, sulfone, phenylene, urea, thiourea, urethane, amine, and a combination thereof. The quencher may be linked to $M^2$ at one or two sites in some embodiments.

In certain embodiments, at least one quencher precursor is used to attach the quenching moiety to at least one polymer. For example, aromatic groups may be used to functionalize a viologen with combinations of boronic acid groups and reactive groups. In certain embodiments, this process includes attaching an aromatic group to each of the two nitrogens in the dipyridyl core of the viologen. At least one boronic acid group, a reactive group, or a combination of the two are then attached to each aromatic group, such that the groups attached to each of the two nitrogens on the dipyridyl core of the viologen may either be the same or different. Certain combinations of the functionalized viologen quenching moiety are described as follows:
  a) a first aromatic group having a pendent reactive group is attached to the first nitrogen and a second aromatic group having at least one pendent boronic group is attached to the second nitrogen;
  b) one or more boronic acid groups are attached to a first aromatic group, which is attached to the first nitrogen, and one boronic acid group and a reactive group are attached to a second aromatic group, which second aromatic group is attached to the second nitrogen;
  c) one boronic acid group and a reactive group are attached to a first aromatic group, which first aromatic group is attached to the first nitrogen, and one boronic acid group and a reactive group are attached to a second aromatic group, which is attached to the second nitrogen; and
  d) one boronic acid group is attached to an aromatic group, which aromatic group is attached to each of the two nitrogens, and a reactive group is attached to a carbon in a heteroaromatic ring in the heteroaromatic centrally located group.

Preferred embodiments comprise two boronic acid moieties and one polymerizable group or coupling group wherein the aromatic group is a benzyl substituent bonded to the nitrogen and the boronic acid groups are attached to the benzyl ring and may be in the ortho- meta- or para-positions.

Figure 5:
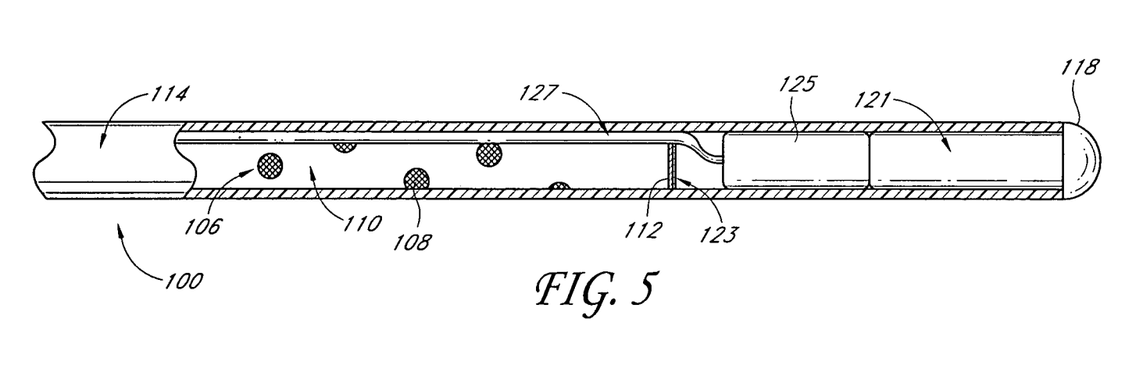
FIG. 5 shows a cut-away view of a sensor where a portion of the porous membrane sheath is cut away to expose the optical fiber and hydrogel beneath the membrane.
Figure 6:
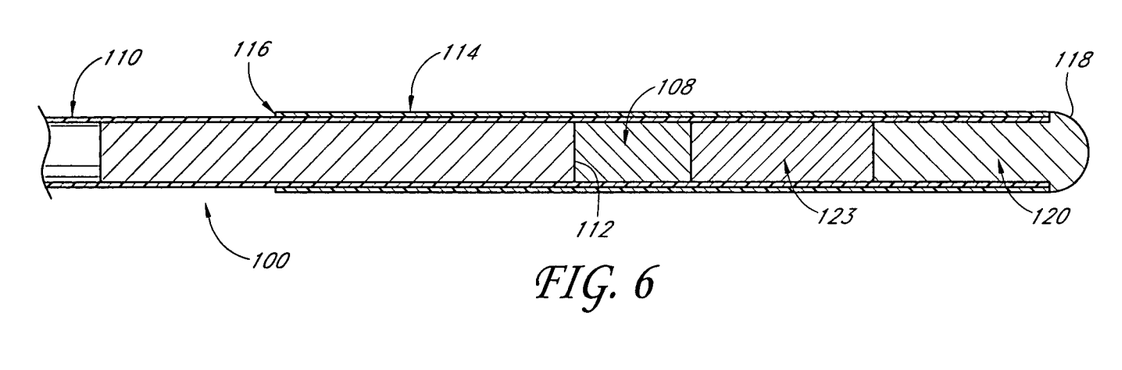
FIG. 6 is a cross-sectional view along a longitudinal axis of a sensor with a hydrogel disposed distal the optical fiber.

FIG. 5 shows an embodiment of the distal portion of a sensor 100 comprising an optical fiber 110 with a distal end 112 disposed in a porous membrane sheath 114. The optical fiber 110 has cavities 106, such as holes, in the fiber-optic wall that can be formed by, for example, mechanical means such as drilling or cutting. The cavities 106 in the optical fiber 110 can be filled with a suitable compound, such as a polymer. In some embodiments, the polymer is a hydrogel 108. In other embodiments of the sensor 100 as shown in FIG. 6, the optical fiber 110 does not have cavities 106, and instead, the hydrogel 108 is disposed in a space distal to the distal end 112 of the optical fiber 110 and proximal to the mirror 123. In some embodiments, the sensor 100 is a glucose sensor. In some embodiments, the glucose sensor is an intravascular or interstitial glucose sensor.

In some embodiments, the porous membrane sheath 114 can be made from a polymeric material such as polyethylene, polycarbonate, polysulfone or polypropylene. Other materials can also be used to make the porous membrane sheath 114 such as zeolites, ceramics, metals, or combinations of these materials. In some embodiments, the porous membrane sheath 114 is microporous and has a mean pore size that is less than approximately two nanometers. In other embodiments, the porous membrane sheath 114 is mesoporous and has a mean pore size that is between approximately two nanometers to approximately fifty nanometers. In still other embodiments, the porous membrane sheath 114 is macroporous and has a mean pore size that is greater than approximately fifty nanometers.

In some embodiments as shown in FIG. 6, the porous membrane sheath 114 is attached to the optical fiber 110 by a connector 116. For example, the connector 116 can be an elastic collar that holds the porous membrane sheath 114 in place by exerting a compressive force on the optical fiber 110. In other embodiments, the connector 116 is an adhesive or a thermal weld.

In some embodiments as shown in FIG. 5, a mirror 123 and thermistor 125 can be placed within the porous membrane sheath 114 distal the distal end 112 of the optical fiber 110. Thermistor leads 127 can be made to run in a space between the optical fiber 110 and porous membrane sheath 114. Although a thermistor 125 is shown, other devices such as a thermocouple, pressure transducer, an oxygen sensor, a carbon dioxide sensor or a pH sensor for example can be used instead.

In some embodiments as shown in FIG. 6, the distal end 118 of the porous membrane sheath 114 is open and can be sealed with, for example, an adhesive 120. In some embodiments, the adhesive 120 can comprise a polymerizable material that can fill the distal end 118 and then be polymerized into a plug. Alternatively, in other embodiments the distal end 118 can be thermally welded by melting a portion of the polymeric material on the distal end 118, closing the opening and allowing the melted polymeric material to resolidify. In other embodiments as shown in FIG. 5, a polymeric plug 121 can be inserted into the distal end 118 and thermally heated to weld the plug to the porous membrane sheath 114. Thermoplastic polymeric materials such as polyethylene, polypropylene, polycarbonate and polysulfone are particularly suited for thermal welding. In other embodiments, the distal end 118 of the porous membrane sheath 114 can be sealed against the optical fiber 110.

Figure 7A:
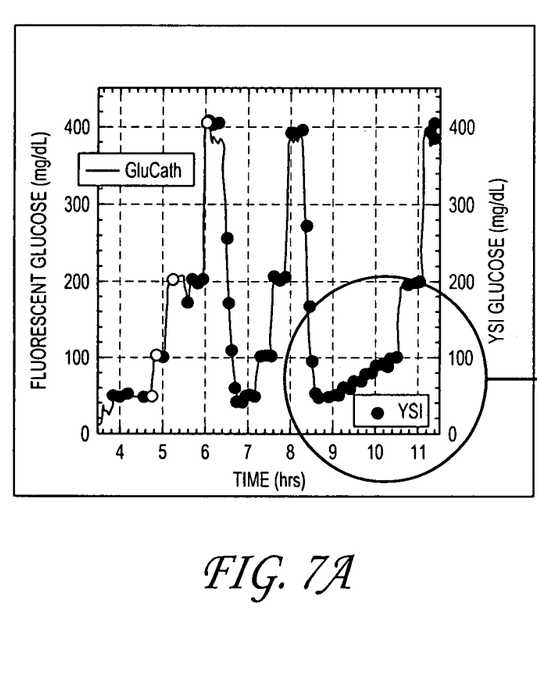
FIGS. 7A and 7B show blood glucose determinations in vitro in a circulating blood loop, with a comparison of the GLUCATH™ and YSI detection methods.
Figure 7B:
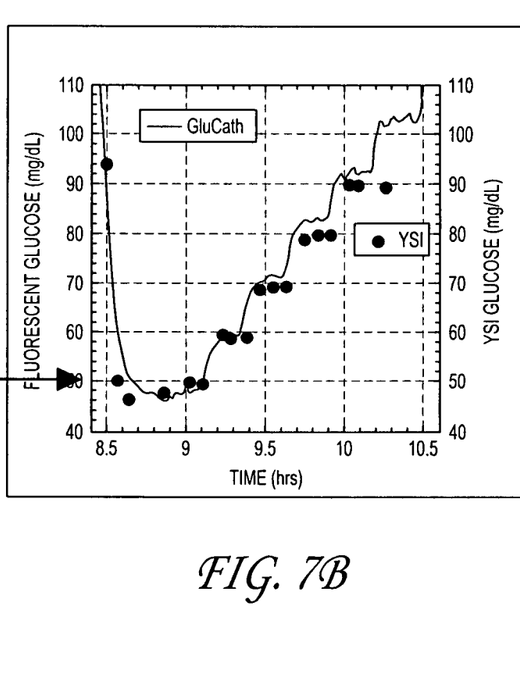

With reference to FIGS. 7A and B, the results of glucose determination over time and with infused glucose in a circulating blood loop in vitro are compared for a continuous glucose sensor in accordance with a preferred embodiment of the present invention (-GLUCATH™) and the Yellow Springs Instrument glucose oxidase lab analyzer (● YSI), the gold standard of blood glucose measurements. The GLUCATH™ equilibrium fluorescence glucose sensor used in this experiment comprised HPTS-triCysMA dye and 3,3'-oBBV quencher. FIG. 7A shows an 8 hr time course with changes in circulating glucose in the range of 50-400 mg/dl. FIG. 7B is an expanded illustration of the two hr stepwise addition of 10 mg/dl boluses. The data show that the equilibrium fluorescence glucose sensor provides continuous monitoring of blood glucose which is as accurate as the YSI lab analyzer. The expanded view in FIG. 7B shows rapid and accurate sensing even at very low levels of blood glucose (between 50 and 100 mg/dl). This is surprising since accurate detection in such a low range has been extremely difficult to accomplish with other detection devices. The lack of accurate and reliable blood glucose sensing below 100 mg/dl has hampered ICU attempts to maintain target blood glucose levels, because of the significant clinical risk of going too low.

Figure 8A:
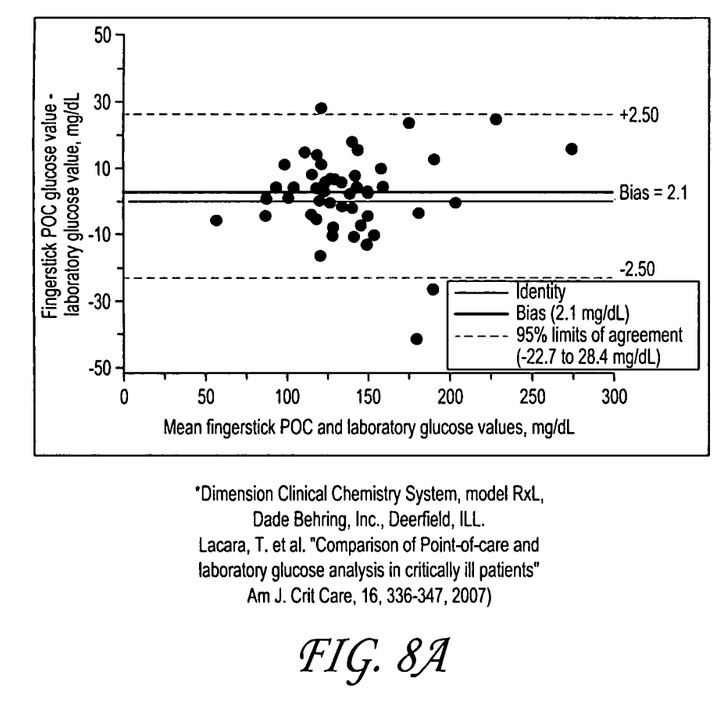
FIGS. 8A and 8B show Bland-Altman difference plots comparing laboratory references to SURESTEP PRO FINGERSTICK™ and GLUCATH™ equilibrium fluorescent glucose sensor. The GLUCATH™ sensor is deployed in vivo in the right jugular vein of sheep.
Figure 8B:
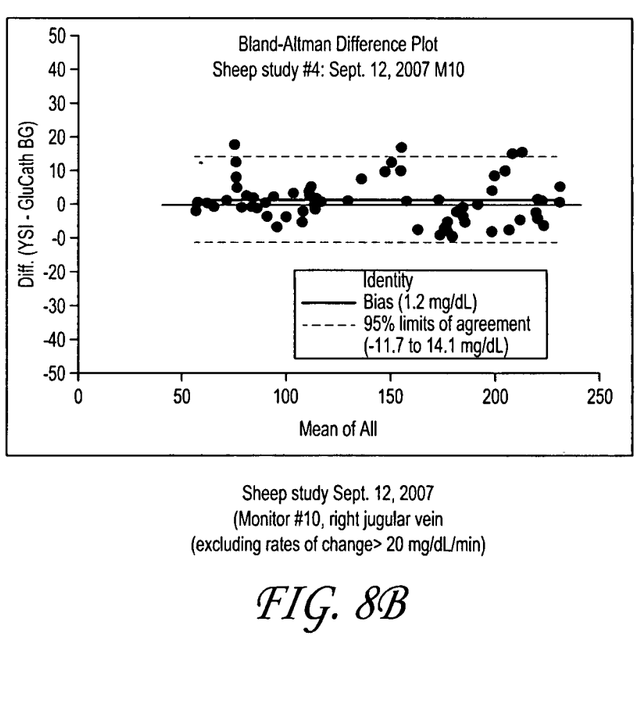

With reference to FIGS. 8A and B, Bland-Altman plots show differences between laboratory references and either fingerstick POC (FIG. 8A) or GLUCATH™ indwelling equilibrium fluorescence glucose sensor (FIG. 8B) for in vivo blood glucose monitoring. FIG. 8A shows results of blood glucose detection using a standard fingerstick test compared to a clinical chemistry system. The 95% confidence limits vary from −22.7 to 28.4 mg/dl with a bias of 2.1 mg/dl. It is noteworthy that very few readings below 100 mg/dl can be seen. FIG. 8B shows results of blood glucose detection using GLUCATH™ continuous equilibrium fluorescence glucose sensor, deployed intravascularly in sheep compared to the YSI lab analyzer. The differences are much tighter, with 95% confidence limits of −11.7 to 14.1 mg/dl and a bias of only 1.2 mg/dl. There are many more data points below 100 mg/dl.

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A method for continuous monitoring of blood analyte levels in a critically ill patient, comprising:
    providing an introducer assembly comprising a hypodermic needle slidably engaged within a removable cannula, wherein a piercing tip of the hypodermic needle extends distally beyond the removable cannula, and wherein the removable cannula is configured to slidably engage an optical analyte sensor;
    inserting the introducer assembly into a vein or artery;
    retracting the hypodermic needle from the removable cannula, while leaving the removable cannula in the vein or artery;
    inserting the optical analyte sensor through the removable cannula and into the vein or artery, wherein the optical analyte sensor comprises an optical fiber having a chemical indicator system disposed along a distal end region thereof, a mirror and a thermistor or thermocouple disposed along the distal end region of the optical fiber, and an optical coupling disposed along a proximal end region thereof, wherein the chemical indicator system is configured to generate an optical signal related to the blood analyte level;
    retracting the removable cannula from the vein or artery, while leaving the optical analyte sensor in the vein or artery;
    removing the removable cannula from the sensor;
    connecting the optical coupling to a device comprising a light source and a detector; and
    detecting the optical signal to monitor the blood analyte level of the critically ill patient.

2. The method of claim 1, wherein the optical analyte sensor comprises an anti-thrombogenic coating or surface treatment.

3. The method of claim 1, wherein the optical analyte sensor has a surface comprising polytetrafluoroethylene.

4. The method of claim 1, wherein removing the removable cannula comprises at least one of splitting the removable cannula, peeling the removable cannula, and cutting the removable cannula.

5. The method of claim 4, wherein removing the removable cannula comprises squeezing a first wing and a second wing together, wherein the first wing and the second wing are disposed opposite each other along a longitudinal axis of the removable cannula.

6. The method of claim 1, wherein the hypodermic needle comprises a flashback chamber, wherein the flashback chamber fills with blood when the blood vessel is cannulated.

7. The method of claim 6, wherein the hypodermic needle comprises a filter, wherein the filter contains the blood within the flashback chamber when the blood vessel is cannulated.

8. The method of claim 1, wherein the hypodermic needle has a diameter less than a diameter of the removable cannula.

9. The method of claim 1, wherein the removable cannula has a proximal end and a distal end, wherein the distal end of the cannula is beveled.

10. The method of claim 1, wherein withdrawing the removable cannula from the blood vessel while leaving the sensor in the blood vessel forms a seal around the sensor.

11. The method of claim 1, wherein the chemical indicator system comprises a fluorophore configured to generate an emission signal in response to excitation light, and an analyte binding moiety operably coupled to the fluorophore, wherein the analyte binding moiety is configured to bind analyte and modulate the emission signal of the fluorophore in a manner related to the amount of analyte binding.

12. The method of claim 11, wherein the chemical indicator system further comprises a water-insoluble polymer matrix, and wherein the fluorophore is covalently bonded to the polymer matrix.

13. The method of claim 11, wherein the analyte binding moiety comprises an aromatic boronic acid covalently bonded to a viologen.

14. The method of claim 1, wherein the optical analyte sensor further comprises a porous membrane disposed along the distal end region of the optical fiber.

15. The method of claim 14, wherein the porous membrane can comprise a material selected from the group consisting of polyethylene, polycarbonate, polysulfone and polypropylene.

16. The method of claim 14, wherein the porous membrane is microporous and has a mean pore size that is less than two nanometers.

17. The method of claim 11, wherein the fluorophore comprises HPTS-triCysMA and the analyte binding moiety comprises 3,3'-oBBV.

\* \* \* \* \*